(12) United States Patent
Guillaume et al.

(10) Patent No.: US 8,440,686 B2
(45) Date of Patent: May 14, 2013

(54) NALMEFENE PRODRUGS

(75) Inventors: Michel Joseph Maurice André Guillaume, Steenokkerzeel (BE); Tim Gaekens, Wilrijk (BE)

(73) Assignee: Janssen Pharmaceutica NV, Beerse (BE)

( * ) Notice: Subject to any disclaimer, the term of this patent is extended or adjusted under 35 U.S.C. 154(b) by 162 days.

(21) Appl. No.: 12/937,744

(22) PCT Filed: Apr. 23, 2009

(86) PCT No.: PCT/EP2009/054882
§ 371 (c)(1),
(2), (4) Date: Oct. 14, 2010

(87) PCT Pub. No.: WO2009/130272
PCT Pub. Date: Oct. 29, 2009

(65) Prior Publication Data
US 2011/0034502 A1  Feb. 10, 2011

(30) Foreign Application Priority Data
Apr. 24, 2008  (EP) ..................... 08155094

(51) Int. Cl.
*A61K 31/485* (2006.01)
*C07D 489/08* (2006.01)
(52) U.S. Cl.
USPC ........................................... 514/282; 546/44
(58) Field of Classification Search .................. 514/282; 546/44
See application file for complete search history.

(56) References Cited

FOREIGN PATENT DOCUMENTS
EP        0615756 B1    6/2001
WO       WO 03/070191 A1   8/2003

OTHER PUBLICATIONS

Hahn, E., et al. "Narcotic Antagonists. 4. Carbon-6 Derivatives of N-Substituted Noroxymorphones as Narcotic Antagonists", Journal of Medicinal Chemistry (1975) vol. 18, No. 3. pp. 259-262.
Mason, B., et al. "A Double-Blind, Placebo-Controlled Pilot Study to Evaluate the Efficacy and Safety of Oral Nalmefene HCl for Alcohol Dependence", Alcoholism: Clinical and Experimental Research (1994) vol. 18, No. 5, pp. 1162-1167.
Mason, B., et al. "A Double-Blind, Placebo-Controlled Study of Oral Nalmefene for Alcohol Dependence", Arch Gen. Psychiatry (1999) vol. 56, pp. 719-724.

*Primary Examiner* — Charanjit Aulakh
(74) *Attorney, Agent, or Firm* — Thomas J. Dodd

(57) ABSTRACT

The present invention relates to ester prodrugs of nalmefene of formula (I), pharmaceutical compositions comprising these compounds, chemical processes for preparing these compounds and their use in the treatment of substance abuse disorders such as alcohol abuse and alcohol dependence and impulse control disorders such as pathological gambling and addiction to shopping.

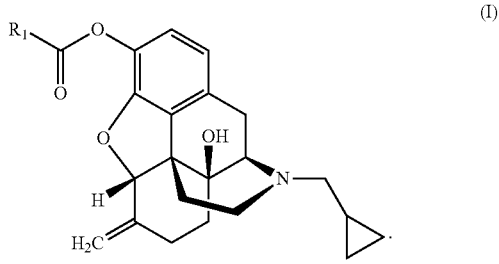

10 Claims, 1 Drawing Sheet

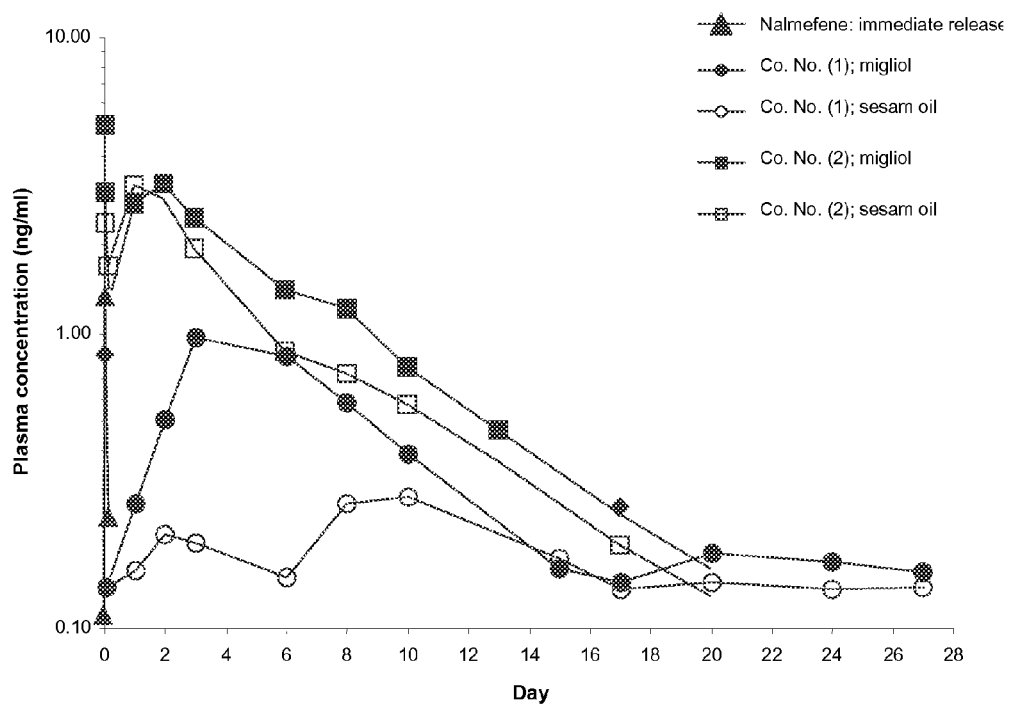
plasma concentration of nalmefene (ng/ml) measured over a 28 day period after intramuscular administration of a formulation comprising nalfmene, compound (1) or compound (2)

NALMEFENE PRODRUGS

CROSS REFERENCE TO RELATED APPLICATIONS

This application is a national stage application of Patent Application No. PCT/EP2009/054882, filed Apr. 23, 2009, which in turn claims the benefit of EPO Patent Application No. 08155094.9 filed Apr. 24, 2008. The complete disclosures of the aforementioned related patent applications are hereby incorporated herein by reference for all purposes.

The present invention relates to ester prodrugs of nalmefene of formula (I), pharmaceutical compositions comprising these compounds, chemical processes for preparing these compounds and their use in the treatment of substance abuse disorders such as alcohol abuse and alcohol dependence and impulse control disorders such as pathological gambling and addiction to shopping.

Nalmefene is an opioid receptor antagonist that has been available for several years as Revex® injection for use in reversing opioid effects and for opioid overdose. Nalmefene is also described in literature for the treatment of substance abuse disorders such as alcohol dependence and abuse, and impulse control disorders such as pathological gambling and addiction to shopping. It has the IUPAC name 17-cyclopropylmethyl-4,5α-epoxy-6-methylenemorphinan-3,14-diol and has the following structure:

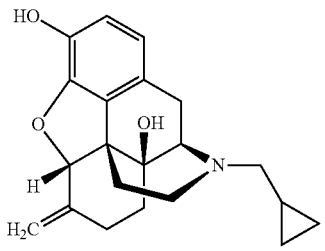

Arch. Gen. Psychiatry, 56, 719-724 (1999), discloses a double-blind, placebo-controlled study for alcohol dependence wherein volunteers were administered orally 20 or 80 mg doses daily for 12 weeks of nalmefene to evaluate safety and efficacy.

Alcoholism: Clinical and Experimental Research, 31, 1179-1187 (2007), describes a multisite, randomized double-blind study of heavy drinkers who were instructed to take 10 to 40 mg nalmefene orally when they believed drinking to be imminent. The study concluded that nalmefene appears to be effective and safe in reducing heavy drinking.

EP-0,250,796 discloses aliphatic, aromatic, carbonate, carbamate and sulfonate ester prodrugs of a number of 3-hydroxymorphinans which are devoid of a bitter taste and therefore suitable for use in oral administration such as buccal, nasal or sublingual administration.

WO-03/070191 discloses a tamper-resistant transdermal delivery device for use in the treatment or prevention of pain comprising an opioid. The disclosed delivery device also comprises an acyl opioid antagonist that is released when an abuser tampers with the device in an effort to extract the opioid from the delivery device. The opioid antagonist thereby blunts or inhibits the euphoric effects of the opioid.

Unfortunately, the commercially used formulations of nalmefene only yield therapeutically effective plasma levels during a limited time interval. Long-acting nalmefene dosage forms would be valuable in therapy and would enhance patient compliance which is very important in the treatment of substance abuse disorders and impulse control disorders.

It has now been found that the nalmefene prodrug compounds of formula (I) provide for therapeutically relevant plasma levels of nalmefene over a prolonged period of time. When the compounds of formula (I) are administered intramuscularly they can provide therapeutically relevant plasma levels of nalmefene over a period of several weeks up to several months. Also when the compounds of formula (I) are administered orally they can provide therapeutically relevant plasma levels of nalmefene over a period of several days.

The present invention relates to a compound of formula (I)

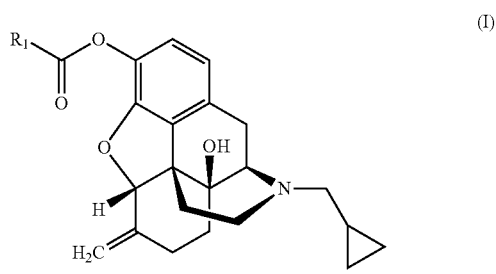

including any stereochemically isomeric form thereof, wherein $R^1$ is $C_{6-16}$alkyl or $C_{8-12}$alkylamino;

or a pharmaceutically acceptable acid addition salt thereof, or a solvate thereof.

As used in the foregoing definitions:

$C_{8-12}$alkyl defines straight and branched chain saturated hydrocarbon radicals having from 8 to 12 carbon atoms such as, for example, octyl, nonyl, decyl, undecyl, dodecyl and the like; —$C_{6-16}$alkyl defines straight and branched chain saturated hydrocarbon radicals having from 6 to 16 carbon atoms such as, for example, hexyl, heptyl, octyl, nonyl, decyl, undecyl, dodecyl, tridecyl, tetradecyl, pentadecyl, and hexadecyl and the like;

$C_{13-16}$alkyl defines straight and branched chain saturated hydrocarbon radicals having from 13 to 16 carbon atoms such as, for example, tridecyl, tetradecyl, pentadecyl, and hexadecyl and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

A prodrug is a pharmacological substance (drug) that is administered in an inactive (or significantly less active) form. Once administered, the prodrug is metabolised in vivo into its active parent drug. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

In an embodiment, the present invention relates to compounds of formula (I) wherein $R^1$ is $C_{13-16}$alkyl or $C_{8-12}$alkylamino.

In another embodiment, the present invention relates those compounds of formula (I) wherein one or more of the following restrictions apply:

a) $R^1$ is $C_7$alkyl, $C_9$alkyl, $C_{11}$alkyl, or $C_{15}$alkyl; or b) $R^1$ is n-heptyl, n-nonyl, n-undecyl, or n-pentadecyl; or c) $R^1$ is $C_{10}$alkylamino; or d) $R^1$ is n-decylamino Compounds of formula (I-a), defined as compounds of formula (I) wherein $R^1$ represents $C_{6-16}$alkyl, can be prepared by art-known esterification methods by reacting nalmefene (II) with an acyl halide of formula (III) in the presence of a base to pick up the acid liberated during the reaction. The $R^1$ substituent in the acyl halide of formula (III) is defined as $C_{6-16}$alkyl.

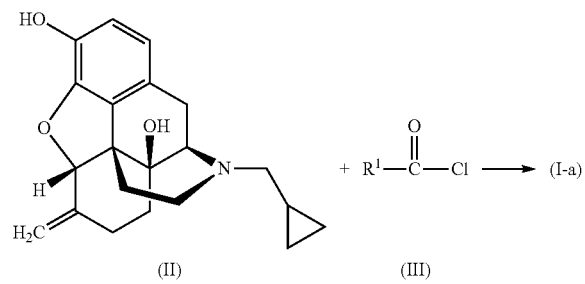

Compounds of formula (I-b), defined as compounds of formula (I) wherein $R^1$ represents $C_{8-12}$alkylamino, can be prepared by reacting nalmefene (II) with an isocyanate of formula (IV).

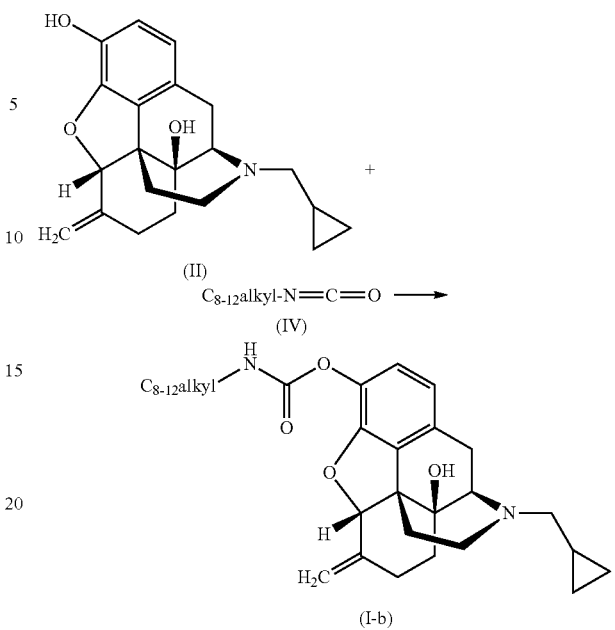

The compounds of the present invention show the advantage of being a long acting opioid receptor antagonist for use in the treatment of substance abuse disorders such as alcohol abuse and alcohol dependence and impulse control disorders such as pathological gambling and addiction to shopping. This can be evidenced, for example, by measuring the plasma levels after intramuscular administration to dogs as demonstrated in Example C.1.

Also oral administration of a prodrug compound of formula (I) has demonstrated that plasma levels of nalmefene can be measured for more than 8 days after administration of a prodrug compound of formula (I) compared to a few hours when nalfmene itself was administered orally.

Hence, the compounds of the present invention allow administration at relatively large time intervals, e.g. at several days, weeks up to several months, the actual time of administration depending on the physical nature of the compound used, the administration route, the composition of the pharmaceutical dosage form and the condition of the subject to be treated. Consequently, the present compounds allow for a more efficient therapy: the sustained release of nalmefene facilitates maintaining a stable plasma concentration at a non-toxic, therapeutically effective level and the route of administration enhances compliance of the subject to be treated with the prescribed medication. Accordingly the compounds of the present invention can be used as a medicament having a sustained release, or as a sustained release medicament.

By the expression "therapeutically relevant" or "therapeutically effective" plasma levels of nalmefene, one means that the plasma level of nalmefene (free nalmefene liberated from the prodrugs of formula (I) of the present invention) should be above approximately 0.1 ng/ml.

Therefore the present compounds of formula (I), or a pharmaceutically acceptable acid addition salt thereof or a solvate thereof, may be used as a medicine, in particular may be used as a medicine for the treatment of substance abuse disorders such as alcohol dependence and alcohol abuse, and impulse control disorders such as pathological gambling and addiction to shopping. Also the compounds of formula (I) may be used as a medicine for decreasing alcohol craving and consumption in alcohol-dependent patients, and for the reduction of alcohol consumption in alcohol-dependent patients.

The present invention also provides the use of a compound of formula (I) or a pharmaceutically acceptable salt thereof for the manufacture of a medicament for the treatment of substance abuse disorders such as alcohol dependence and alcohol abuse, and impulse control disorders such as pathological gambling and addiction to shopping.

Further, the present invention provides a method of treatment of substance abuse disorders or impulse control disorders in a mammalian subject, which comprises administering to a mammal in need of such treatment a therapeutically effective amount of a compound of formula (I) or a pharmaceutically acceptable salt thereof Substance abuse disorders include alcohol dependence and alcohol abuse. Impulse control disorders include pathological gambling and addition to shopping.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in free base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel, Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use. Formulations for intramuscular or subcutaneous administration are of particular interest. Such pharmaceutical compositions should cause little or no tissue irritation or inflammation at the place of injection. Suitable solvents are e.g. sesame oil or migliol.

The compounds of formula (I) may also be formulated in rectal compositions such as suppositories or retention enemas, e.g. containing conventional suppository bases such as cocoa butter and/or other glycerides.

EXPERIMENTAL PART

Example B.1

Palmitoyl chloride (16.1 ml, 53.2 mmol) was added dropwise over 30 minutes at ambient temperature to a stirred mixture of nalmefene hydrochloride (20.0 g, 1.0 equivalent), toluene (400 ml, 20 ml/g) and triethylamine (16.3 ml, 2.2 equivalents) under an inert atmosphere. Stirring at ambient temperature was continued for 16 hours. Afterwards the reaction mixture was washed with water (400 ml, 20 ml/g). After phase separation the organic layer was dried with magnesium sulfate, filtered and the filtrate was concentrated under reduced pressure. Yield: 30.8 g (95%).

NMR:
$^1$H NMR (400 MHz, DMSO-d6) δ ppm 0.08-0.16 (m, 2H) 0.43-0.53 (m, 2H) 0.81-0.89 (m, 4H) 1.14-1.42 (m, 26H) 1.53 (dt, J=12.78, 3.65, 3.46 Hz, 1H) 1.59-1.67 (m, J=7.55, 7.55, 7.55, 7.55 Hz, 2H) 1.96 (td, J=12.02, 3.65 Hz, 1H) 2.07 (dt, J=13.66, 3.08, 2.90 Hz, 1H) 2.24 (td, J=12.53, 4.91 Hz, 1H) 2.35 (t, J=6.04 Hz, 2H) 2.43-2.49 (m, 1H) 2.54 (t, J=7.43 Hz, 2H) 2.53-2.61 (m, 1H) 2.62-2.68 (m, 1H) 3.03 (dd, J=12.09, 6.55 Hz, 2H) 4.80 (d, J=1.76 Hz, 1H) 4.91 (br. s., 1H) 4.96 (s, 1H) 5.05 (d, J=1.26 Hz, 1H) 6.66 (d, J=8.06 Hz, 1H) 6.77 (d, J=8.31 Hz, 1H)

LC-MS:
HR-MS (ES$^+$): Calculated for $C_{37}H_{56}NO_4^+$: 578.4209, Found: 578.4199.

Elemental Analysis:
Anal. Calcd for $C_{37}H_{55}NO_4$: C: 76.91; H: 9.59; N: 2.42. Found: C: 77.01; H: 9.96; N: 1.89.

Example B.2

A suspension of nalmefene hydrochloride (20.0 g, 53.2 mmol), toluene (400 ml, 20 ml/g), triethylamine (8.9 ml, 1.2 equivalent) and decyl isocyanate (13.3 ml, 1.2 equivalent) was refluxed for 16 hours. Three more portions of decyl isocyanate were added (respectively 2.2 ml, 0.2 equivalent; 2.2 ml, 0.2 equivalent and 4.4 ml, 0.4 equivalent) during the next 24 hours of reflux. After the reaction mixture was cooled to ambient temperature, it was washed with water (400 ml, 20 ml/g). The organic layer was dried with magnesium sulfate, filtered and concentrated under reduced pressure. The residue was purified by column chromatography (Silica 60 Å 25-40 μg, 100% ethyl acetate), yielding 17.4 g (63%) of compound (2).

NMR:
$^1$H NMR (400 MHz, DMSO-d6) δ ppm 0.06-0.17 (m, 2H) 0.41-0.53 (m, 2H) 0.78-0.91 (m, 4H) 1.22-1.31 (m, 16H) 1.40-1.48 (m, 2H) 1.52 (dt, J=12.78, 3.56 Hz, 1H) 1.97 (td, J=11.96, 3.53 Hz, 1H) 2.06 (dt, J=13.60, 3.53 Hz, 1H) 2.23 (td, J=12.46, 5.04 Hz, 1H) 2.35 (dd, J=6.29, 3.78 Hz, 2H) 2.43-2.49 (m, 1H) 2.56 (dd, J=18.88, 5.79 Hz, 1H) 2.65 (dd, J=11.71, 4.15 Hz, 1H) 2.97-3.08 (m, 4H) 4.79 (d, J=1.51 Hz, 1H) 4.90 (s, 1H) 4.94 (s, 1H) 5.10 (d, J=1.01 Hz, 1H) 6.62 (d, J=8.06 Hz, 1H) 6.75 (d, J=8.31 Hz, 1H) 7.63 (t, J=5.67 Hz, 1H)

LC-MS:
HR-MS (ES$^+$): Calculated for $C_{32}H_{47}N_2O_4^+$: 523.3536, Found: 523.3517.

Elemental Analysis:
Anal. Calcd for $C_{32}H_{46}N_2O_4$: C, 73.53; H, 8.87; N, 5.36. Found: C, 74.73; H, 9.45; N, 5.58.

Example B.3

Octanoyl chloride (2.27 ml, 13.3 mmol) was added dropwise over 30 minutes at ambient temperature to a stirred mixture of nalmefene hydrochloride (5 g, 1.0 equivalent), toluene (100 ml, 20 ml/g) and triethylamine (4.08 ml, 2.2 equivalents) under an inert atmosphere. Stirring at ambient temperature was continued for 16 hours. 0.15 ml (0.07 equivalent) octanoyl chloride was added extra. The solution was stirred for 4 more hours at ambient temperature to complete the conversion. Afterwards the reaction mixture was washed with water (400 ml, 20 ml/g). After phase separation the organic layer was dried with magnesium sulfate, filtered and the filtrate was concentrated under reduced pressure, yielding 5.98 g (96%) of compound (3).

NMR:
1H NMR (400 MHz, DMSO-d$_6$) δ ppm 0.02-0.18 (m, 2H) 0.38-0.55 (m, 2H) 0.76-0.94 (m, 4H) 1.18-1.41 (m, 10H) 1.53 (dt, J=12.78, 3.30 Hz, 1H) 1.58-1.70 (m, 2H) 1.96 (td, J=12.09, 3.78 Hz, 1H) 2.07 (dt, J=13.72, 3.15, 3.02 Hz, 1H) 2.24 (td, J=12.59, 5.04 Hz, 1H) 2.31-2.40 (m, 2H) 2.45-2.50 (m, 1H) 2.54 (t, 2H) 2.53-2.61 (m, 1H) 2.65 (dd, J=11.83, 4.28 Hz, 1H) 3.03 (dd, J=12.09, 6.55 Hz, 2H) 4.80 (d, J=1.76 Hz, 1H) 5.03 (br. s., 1H) 4.96 (s, 1H) 5.05 (d, J=1.26 Hz, 1H) 6.66 (d, J=8.31 Hz, 1H) 6.76 (d, J=8.06 Hz, 1H)

LC-MS:
HRMS (ES+): Calculated for $C_{29}H_{39}NO_4^+$: 466.2957, Found: 466.2967.

Example B.4

Decanoyl chloride (2.77 ml, 13.3 mmol) was added dropwise over 30 minutes at ambient temperature to a stirred mixture of nalmefene hydrochloride (5 g, 1.0 eq.), toluene (100 ml, 20 ml/g) and triethylamine (4.08 ml, 2.2 eq.) under an inert atmosphere. Stirring at ambient temperature was continued for 16 hours. Afterwards the reaction mixture was washed with water (400 ml, 20 ml/g). After phase separation the organic layer was dried with magnesium sulfate, filtered and the filtrate was concentrated under reduced pressure, yielding 6.31 g (96%) of compound (4).

NMR:
1H NMR (400 MHz, DMSO-d$_6$) δ ppm 0.09-0.15 (m, 2H) 0.43-0.52 (m, 2H) 0.82-0.89 (m, 4H) 1.15-1.42 (m, 14H) 1.53 (dt, J=12.84, 3.40 Hz, 1H) 1.63 (quin, J=7.30 Hz, 2H) 1.96

(td, J=12.09, 3.78 Hz, 1H) 2.07 (dt, J=13.60, 3.27 Hz, 1H) 2.24 (td, J=12.53, 5.16 Hz, 1H) 2.30-2.40 (m, 2H) 2.44-2.49 (m, 1H) 2.54 (t, J=7.55 Hz, 2H) 2.53-2.61 (m, 1H) 2.65 (dd, J=11.83, 4.28 Hz, 1H) 3.03 (dd, J=12.09, 6.55 Hz, 2H) 4.96 (br. s., 1H) 4.80 (d, J=1.76 Hz, 1H) 4.97 (s, 1H) 5.05 (d, J=1.51 Hz, 1H) 6.66 (d, J=8.06 Hz, 1H) 6.75-6.78 (m, 1H).

LC-MS:

HRMS (ES+): Calculated for $C_{31}H_{43}NO_4^+$: 494.3270, Found: 494.3265.

Example B.5

Dodecanoyl chloride (3.12 ml, 13.3 mmol) was added dropwise over 30 minutes at ambient temperature to a stirred mixture of nalmefene hydrochloride (5 g, 1.0 eq.), toluene (100 ml, 20 ml/g) and triethylamine (4.08 ml, 2.2 eq.) under an inert atmosphere. Stirring at ambient temperature was continued for 16 hours. Afterwards the reaction mixture was washed with water (400 ml, 20 ml/g). After phase separation the organic layer was dried with magnesium sulfate, filtered and the filtrate was concentrated under reduced pressure, yielding 6.36 g (92%) of compound (5).

NMR:

1H NMR (400 MHz, DMSO-$d_6$) δ ppm 0.08-0.16 (m, 2H) 0.44-0.51 (m, 2H) 0.81-0.89 (m, 4H) 1.15-1.42 (m, 18H) 1.53 (dt, J=12.78, 3.30 Hz, 1H) 1.63 (quin, J=7.43 Hz, 2H) 1.96 (td, J=12.09, 3.53 Hz, 1H) 2.06 (dt, J=13.60, 3.15 Hz, 1H) 2.24 (td, J=12.46, 5.04 Hz, 1H) 2.29-2.40 (m, 2H) 2.45-2.49 (m, 1H) 2.53 (t, J=7.68 Hz, 2H) 2.53-2.60 (m, 1H) 2.65 (dd, J=11.96, 4.41 Hz, 1H) 3.03 (dd, J=11.96, 6.67 Hz, 2H) 4.99 (br. s., 1H) 4.80 (d, J=1.76 Hz, 1H) 4.96 (s, 1H) 5.05 (d, 1H) 6.66 (d, J=8.06 Hz, 1H) 6.76 (d, J=8.06 Hz, 1H)

LC-MS:

HRMS (ES+): Calculated for $C_{33}H_{47}NO_4^+$: 522.3583, Found: 522.3590.

TABLE F-1 final compounds

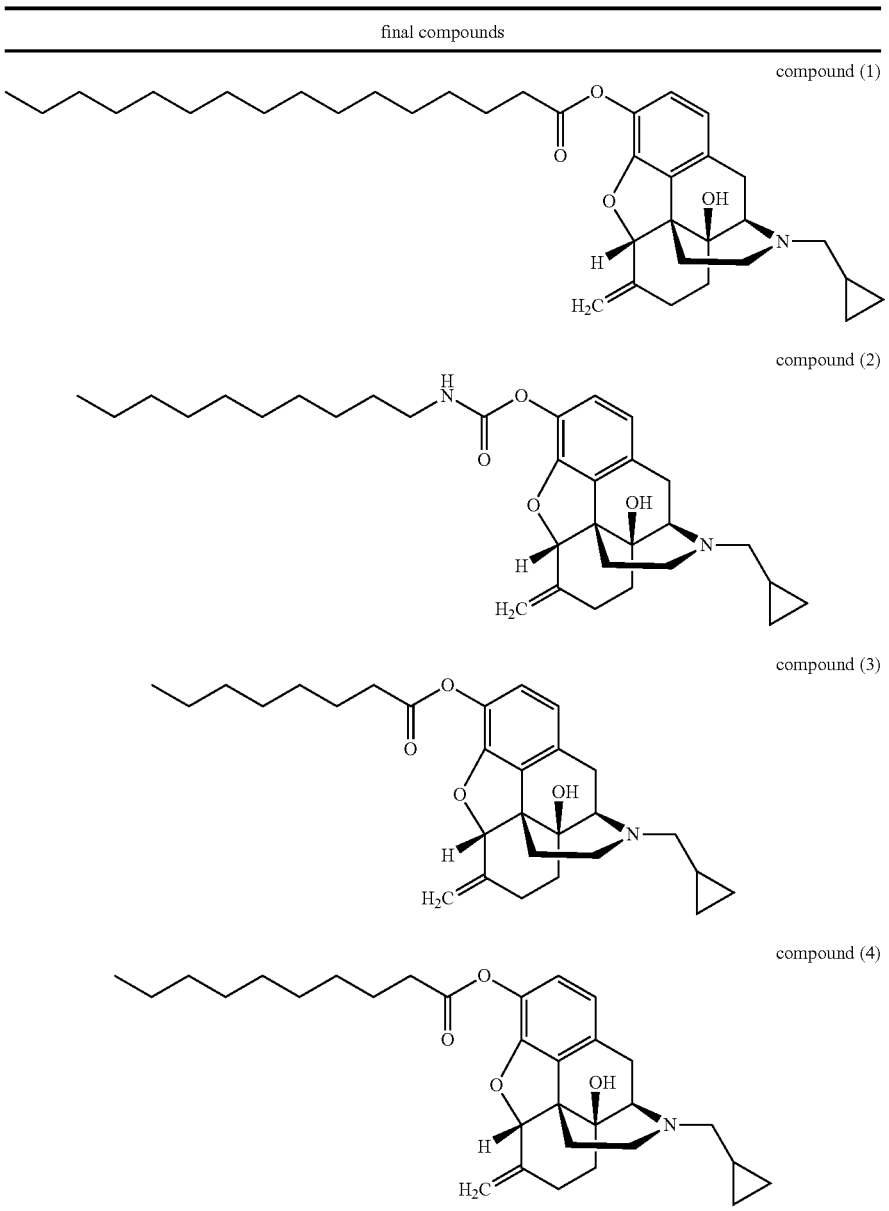

TABLE F-1-continued final compounds compound (5)

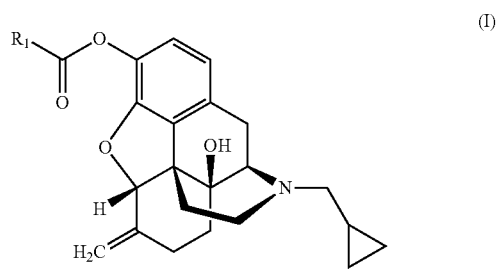

C.1. In vivo PK Studies in Dog (IM Injection): Plasma Levels of Nalmefene

A single intramuscular dose of nalmefene, compound (1) or compound (2) at a concentration of 20 mg nalmefene equivalent/ml in sesam oil or in migliol was given to three dogs per formulation at a dose of 1 mg equivalent nalmefene/kg body weight.

Reference was an immediate release formulation (IR) of nalmefene at a concentration of 0.40 mg/ml in saline, dosed single dose by intramuscular administration (IM) at 0.02 mg equivalent nalmefene/kg body weight.

Blood samples were taken over a period of 27 days after dosing of the prodrug-formulations and over 48 hours after dosing the immediate release formulation of nalmefene. Blood samples were processed to obtain plasma. Plasma samples were analysed individually for nalmefene by means of a qualified LC-MS/MS-method.

Phamacokinetic data analysis was performed on the individual plasma concentration profiles by non-compartmental pharmacokinetic analysis using validated WinNonlin software (v. 4.0.1a).

Results:

The plasma profiles of nalmefene (ng/ml) after intramuscular (IM) dosing of compound (1) or of the IR formulation of nalmefene itself are shown in FIG. 1.

Plasma concentration of nalmefene were quantifiable up to 20 days after dosing of compound (2) and up to 27 days after dosing of compound (1).

C.2. In vivo PK Studies in Dog (Oral Administration): Plasma Levels of Nalmefene Doses at 10 mg/kg or 20 mg/kg body weight of a compound of formula (I) or of nalmefene itself in a solution of 20% HP-β-CD (hydroxypropyl-β-cyclodextrines) were used and orally administered to dogs.

Blood samples were taken over a period of 192 hours after oral administration. Blood samples were processed to obtain plasma. Plasma samples were analysed individually for nalmefene by means of a qualified LC-MS/MS-method.

Plasma concentration of nalmefene were quantifiable up to 192 hours after dosing of compound (2).

DESCRIPTION OF THE DRAWINGS

FIG. 1 shows the plasma concentration of nalmefene (ng/ml) measured over a 28 day period after IM administration of a formulation comprising nalfmene and compound (1).

The invention claimed is:

1. A compound of formula (I)

(I)

including any stereochemically isomeric form thereof, wherein $R^1$ is $C_{6-16}$alkyl or $C_{8-12}$alkylamino;

or a pharmaceutically acceptable acid addition salt thereof.

2. The compound as claimed in claim 1 wherein $R^1$ is $C_7$alkyl, $C_9$alkyl, $C_{11}$alkyl, or $C_{15}$alkyl.

3. The compound as claimed in claim 1 wherein $R^1$ is $C_{10}$alkylamino.

4. The compound as claimed in claim 1 wherein the compound is

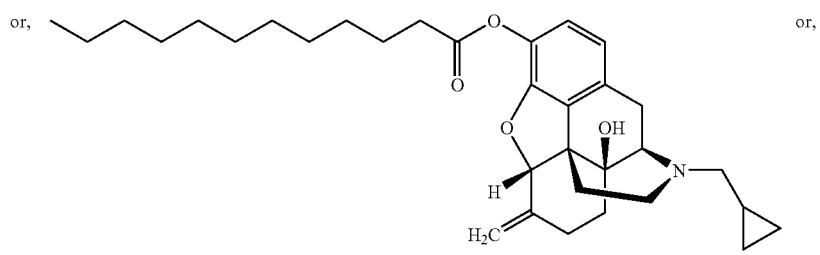

or, or,

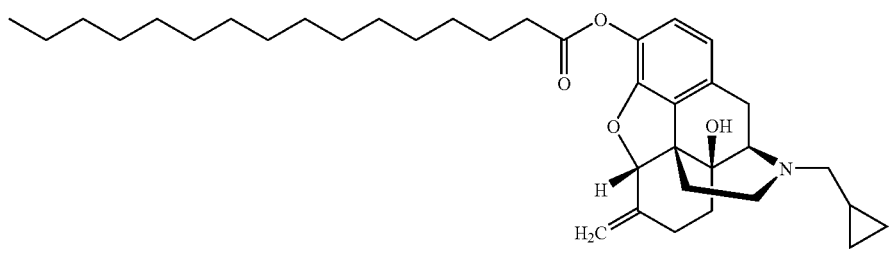

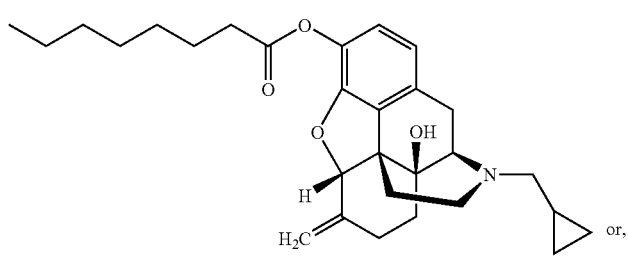

or,

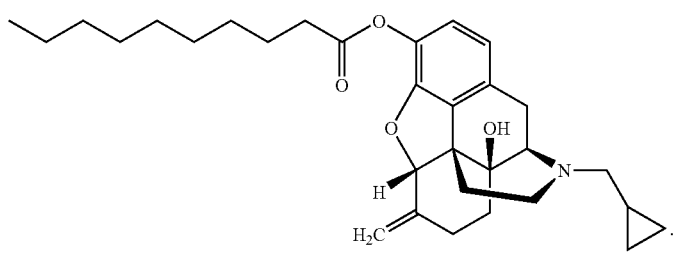

5. The compound as claimed in claim 1 wherein the compound is

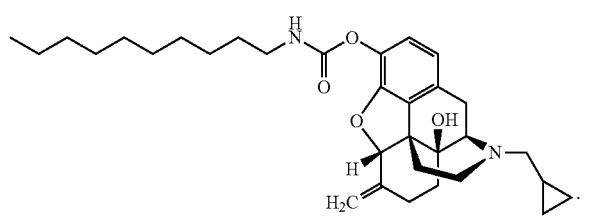

6. A pharmaceutical composition comprising a pharmaceutically acceptable carrier and a therapeutically active amount of the compound claim 1.

7. A process for preparing a pharmaceutical composition as claimed in claim 6 wherein a therapeutically active amount of the compound of formula I is intimately mixed with a pharmaceutically acceptable carrier.

8. A method for treating a patient suffering from alcohol abuse or alcohol dependence, said method comprising administering an effective amount of a compound of claim 1 to said patient.

9. A process for preparing a compound of claim 1 wherein $R^1$ represents $C_{6-16}$alkyl, comprising esterification methods by reacting nalmefene (II) with an acyl halide of formula (III) in the presence of a base to pick up the acid liberated during the reaction,

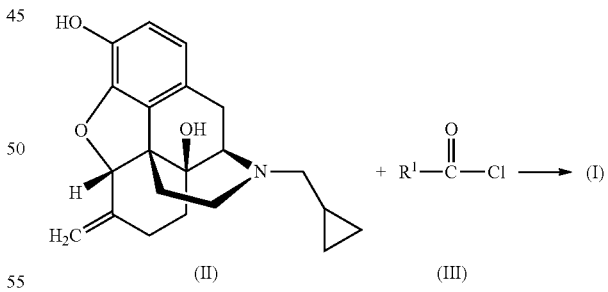

or; if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

10. A process for preparing a compound of formula (I-b), defined as compounds of formula (I) wherein $R^1$ represents $C_{8-12}$alkylamino, comprising reacting nalmefene (II) with an isocyanate of formula (IV),

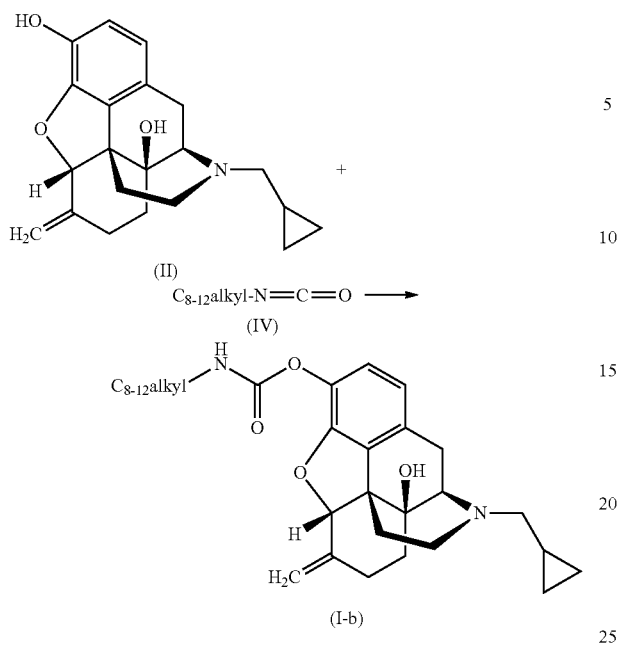
or; if desired; a compound of formula (I-b) is converted into a pharmaceutically acceptable acid addition salt, or conversely, an acid addition salt of a compound of formula (I-b) is converted into a free base form with alkali; and, if desired, preparing stereochemically isomeric forms thereof.
* * * * *